(12) United States Patent
Lee et al.

(10) Patent No.: US 7,173,155 B1
(45) Date of Patent: Feb. 6, 2007

(54) TERPHENYL DIHALIDE MONOMERS HAVING SULFONATE GROUPS AND PROCESS FOR PREPARING THE SAME

(75) Inventors: Jae-Suk Lee, Gwangju (KR);
Sun-Young Chang, Gwangju (KR);
Kwan-Soo Lee, Gwangju (KR);
Myung-Hwan Jeong, Gwangju (KR);
Jung-Eun Yang, Gwangju (KR)

(73) Assignee: Gwangju Institute of Science and Technology, Gwangju (KR)

( * ) Notice: Subject to any disclaimer, the term of this patent is extended or adjusted under 35 U.S.C. 154(b) by 0 days.

(21) Appl. No.: 11/485,855

(22) Filed: Jul. 13, 2006

(30) Foreign Application Priority Data

Jan. 12, 2006 (KR) .................... 10-2006-0003657

(51) Int. Cl.
*C07C 315/00* (2006.01)
(52) U.S. Cl. ........................................ 568/34
(58) Field of Classification Search ............ 568/34
See application file for complete search history.

(56) References Cited

FOREIGN PATENT DOCUMENTS

WO  09804508  *  5/1998

* cited by examiner

*Primary Examiner*—J. Parsa
(74) *Attorney, Agent, or Firm*—Frommer Lawrence & Haug LLP; Ronald R. Santucci (57) ABSTRACT

The present invention relates to a terphenyl dihalide monomer having sulfonate groups and a process for preparing the same. More particularly, the present invention relates to a terphenyl dihalide monomer having sulfonate groups prepared by a process comprising obtaining a terphenyl dihalide derivative by Suzuki cross-coupling of a tetrahalobenzene and phenylboronic acid and introducing sulfonate groups into the phenyl rings at each end of the terphenyl dihalide derivative, the resultant monomer capable of being prepared into a polymer electrolyte having superior ion conductivity through nucleophilic aromatic substitution ($S_NAr$) polymerization due to the presence of two halogen atoms and two conducting sulfonate groups in the monomer molecule, and a process for preparing the same.

5 Claims, 12 Drawing Sheets

(a) —— TPDF
(b) —— TPDF-dept (c) —— STPDF
(d) —— STPDF-dept

(a) – bcm
(b) – dept135

(a) - bcm
(b) - dept135

(c) - bcm
(d) - dept135

Fig. 12

TERPHENYL DIHALIDE MONOMERS HAVING SULFONATE GROUPS AND PROCESS FOR PREPARING THE SAME

This application claims priority benefits from Korean Patent Application No. 10-2006-0003657 filed Jan. 12, 2006.

TECHNICAL FIELD

The present invention relates to a terphenyl dihalide monomer having sulfonate groups and a process for preparing the same. More specifically, the present invention also relates to a terphenyl dihalide monomer having sulfonate groups prepared by the steps of obtaining a terphenyl dihalide derivative by Suzuki cross-coupling of a tetrahalobenzene and phenylboronic acid and introducing sulfonate groups into the phenyl rings at each end of the terphenyl dihalide derivative, the resultant monomer capable of being prepared into a polymer electrolyte having superior ion conductivity through nucleophilic aromatic substitution ($S_NAr$) polymerization due to the presence of two halogen atoms and two conducting sulfonate groups in the monomer molecule, and a process for preparing the same.

BACKGROUND ART

Polymer electrolyte membrane is a novel functional material used in secondary cells, fuel cells, and the like. In general, polymer electrolyte membranes are classified into perfluorinated polymer electrolyte membranes and hydrocarbon polymer electrolyte membranes. Perfluorinated polymer electrolyte membranes are commonly used due to the advantages that they have chemical stability because of the strong carbon-fluorine (C—F) bond and the shielding effect characteristic of the fluorine atom, have superior mechanical properties and, particularly, have superior conductivity as proton exchange membrane. Currently, the most widely used commercially-available polymer electrolyte membrane material is Nafion™ (perfluorinated sulfonic acid polymer) of DuPont, U.S.A. Nafion™, a representative example of commercial proton exchange membrane, is widely used because of superior ion conductivity, chemical stability, ion selectivity, etc. Despite the superior performances, production of perfluorinated polymer electrolyte membranes is rather complicated regarding raw materials and manufacturing process, making it less applicable to industry. Besides, the fluorine atoms contained in the polymer main chain may cause environmental pollution and also generate some toxic substances. Further, they have a high tendency of methanol crossover, or permeation of methanol through the polymer membrane, and polymer membrane capacity is greatly reduced at 80° C. or above.

Numerous researches have been performed to prepare polymer electrolyte membranes through partial modification of Nafion™ or polyaryl-based polymers. However, the polymer electrolyte membranes obtained by polymer modification have the problems of low hydration stability, low proton conductivity, and the like.

Typically, sulfonate-substituted polymer electrolyte membranes are produced by direct copolymerization or post-sulfonation. Both of them make use of nucleophilic aromatic substitution. Direct copolymerization is advantageous in that control of the sulfonate groups introduced to the polymer main chain is easier than post-sulfonation. However, monomers having sulfonate groups are needed to produce polymer electrolyte membranes through direct copolymerization. Typical examples of monomers having sulfonate groups are 3,3'-disulfonated-4,4'-dichlorodiphenylsulfone (SDCDPS), 3,3'-disulfonated-4,4'-difluorodiphenylsulfone (SDFDPS), 5,5'-carbonylbis(2-fluorobenzenesulfonate), etc. However, considering the significant values of polymers having sulfonate groups from the industrial point of view, monomers available for production of such polymers are still far too scarce.

Accordingly, there is an urgent need for the development of new sulfonate-containing materials useful as polymer electrolyte membrane materials.

DISCLOSURE OF THE INVENTION

The present invention relates to sulfonate-containing monomers used to produce polymer electrolyte membranes having improved physical and chemical properties and practically useful for fuel cells.

Therefore, in an embodiment of the present invention there is provided a terphenyl dihalide monomer having sulfonate groups.

In another embodiment of the present invention there is provided a process for preparing the terphenyl dihalide monomer having sulfonate groups.

BRIEF DESCRIPTION OF THE DRAWINGS

The above and other objects, features and advantages of the present invention will be apparent from the following detailed description of the preferred embodiments of the invention in conjunction with the accompanying drawings, in which.

BEST MODE FOR CARRYING OUT THE INVENTION

The present invention relates to a terphenyl dihalide monomer having sulfonate groups represented by the formula (1) below:

(1)

wherein $X^1$ and $X^2$ are independently F or Cl; and $M^1$ and $M^2$ are independently an alkali metal atom.

In the formula (1), each of the sulfonate group ($SO_3M$), the halide group ($X^1$, $X^2$) and the phenyl group may be independently present at the ortho (o-), meta (m-) or para (p-) position of the aromatic rings.

Hereunder is given a more detailed description of the present invention.

The terphenyl dihalide monomer having sulfonate groups represented by the formula (1) has two halogen atoms enabling polymerization and two conducting sulfonate groups. The halogen atoms enable the monomer to be directly copolymerized by nucleophilic aromatic substitution and the conducting sulfonate groups make the so-copolymerized polymer to be useful as electrolyte membrane material.

Indeed, a polymer electrolyte membrane prepared from the monomer of the present invention has significantly superior proton conductivity per cost as compared with Nafion™ (perfluorinated sulfonic acid polymer) (DuPont, USA), while having superior physical properties comparable to other sulfonate-containing polymer electrolyte membranes. Accordingly, the monomer of the present invention is useful for the production of polymer electrolyte membranes for fuel cells.

The present invention is also characterized by a process for preparing the terphenyl dihalide monomer having sulfonate groups represented by the formula (1), which comprises the following two steps as shown in the scheme 1 below:

1) preparing a terphenyl dihalide derivative represented by the formula (2) below by Suzuki cross-coupling of a tetrahalobenzene represented by the formula (3) with phenylboronic acid; and 2) introducing sulfonate groups into the phenyl rings at each end of the terphenyl dihalide derivative represented by the formula (2).

The process for preparing the monomer of the present invention by the scheme 1 is described in further detail.

First, a terphenyl dihalide derivative represented by the formula (2) is prepared by Suzuki cross-coupling of a tetrahalobenzene represented by the formula (3) with phenylboronic acid. The tetrahalobenzene represented by the formula (3), which is used as staring material in the present invention, may be 1,2-dibromo-4,5-difluorobenzene, 1,4-dibromo-2,5-difluorobenzene, etc. The Suzuki cross-coupling reaction is performed by the conventional method in the presence of an alkali metal base and a palladium catalyst, in a temperature range from 60 to 140° C. The alkali metal base may be selected from sodium carbonate, potassium carbonate, sodium hydroxide, potassium hydroxide, etc. The palladium catalyst may be palladium tetrakistriphenylphosphine [Pd(PPh$_3$)$_4$], palladium acetate, palladium chloride, etc. For the reaction solvent, commonly used organic solvent may be used. To be specific, tetrahydrofuran (THF), N,N-dimethylformamide (DMF), toluene, pentane, dioxane, ethylene glycol, dimethyl ether (DME), dimethylacetamide (DMA), etc. may be used.

Next, the terphenyl dihalide derivative represented by the formula (2) is substituted by an adequate sulfonate compound to obtain the terphenyl dihalide monomer having sulfonate groups represented by the formula (1). The sulfonate compound may be selected from, for example, strong sulfuric acid, chlorosulfonic acid (ClSO$_3$H), fuming sulfuric acid (SO$_3$·H$_2$SO$_4$), fuming sulfuric acid triethylphosphate (SO$_3$·TEP), etc. The sulfonate substitution reaction may be performed at from 0 to 100° C.

With two halogen atoms enabling polymerization and two conducting sulfonate groups in one molecule, the novel monomer represented by the formula (1) can be polymerized by nucleophilic aromatic substitution (S$_N$Ar) and the resultant polymer has superior proton conductivity to be used as ionic electrolyte. Thus, the present invention is further characterized by a use of the polymer polymerized from the monomer represented by the formula (1) as ionic electrolyte.

EXAMPLES

Practical and preferred embodiments of the present invention are illustrated as shown in the following examples. However, it will be appreciated that those skilled in the art, in consideration of this disclosure, may make modifications and improvements within the spirit and scope of the present invention.

Example 1

2',5'-Difluoro-[1,1':4',1"]terphenyl (TPDF)

wherein $X^1$ and $X^2$ are independently F or Cl; $Y^1$ and $Y^2$ are independently Br or I; and $M^1$ and $M^2$ are independently an alkali metal atom.

To a 2-necked round flask equipped with a condenser and a magnetic stir bar and substituted with nitrogen, 1,4-dibromo-2,5-difluorobenzene (18.39 mmol), phenylboronic acid (44.14 mmol), tetrahydrofuran (100 mL), a 2M potassium carbonate solution (50 mL), and then, a palladium tetrakistriphenylphosphine [Pd(PPh$_3$)$_4$; 5 mol %] catalyst were added. Reaction was performed under nitrogen atmosphere at 80° C. for 8 hours. Upon completion of the reaction, extraction was performed using dichloromethane and the extract was washed several times with water. Then, water was removed with magnesium sulfate. Dichloromethane remaining in the filtrate was removed using a vacuum evaporator and unreacted material was removed by column chromatography. Then, recrystallization was performed using dichloromethane to obtain more pure final product. The product was dried under vacuum at 60° C. The yield was relatively high (≧92%).

Figure 1:
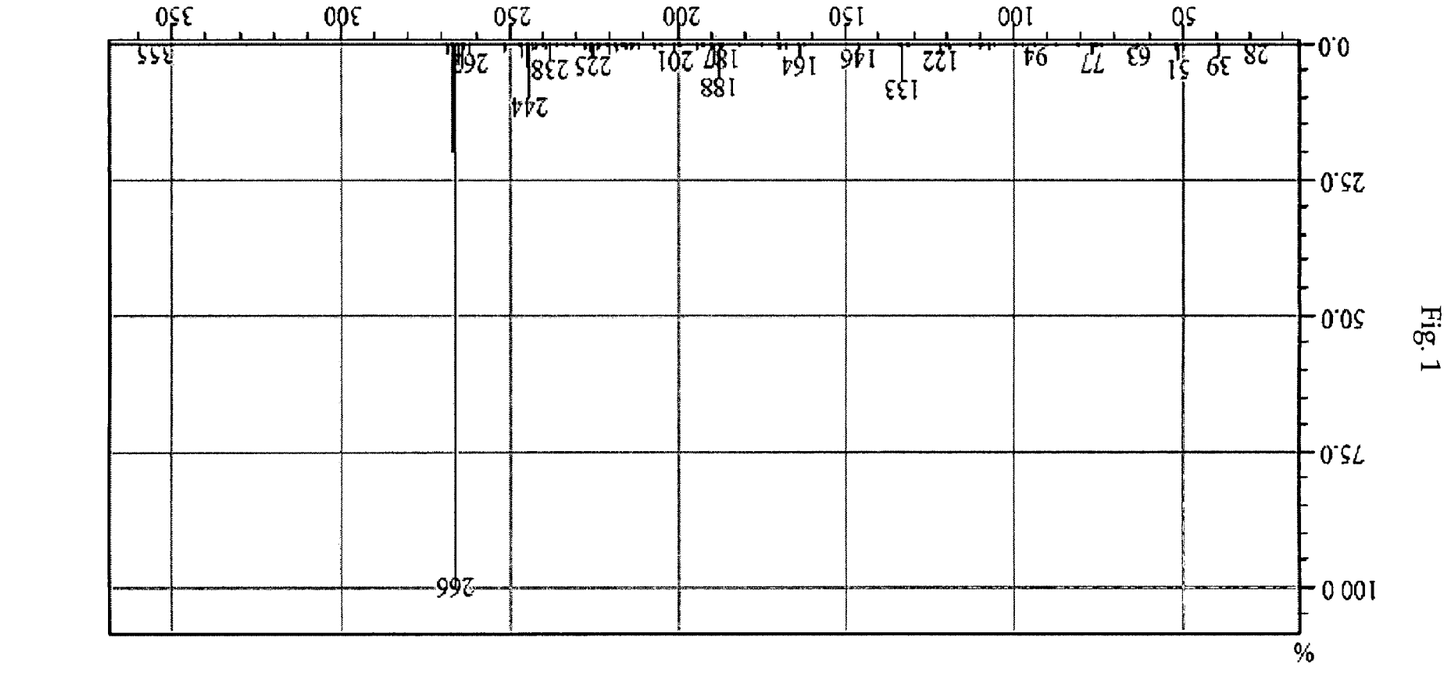
FIG. 1 shows a GC-Mass spectrum of TPDF.
Figure 2:
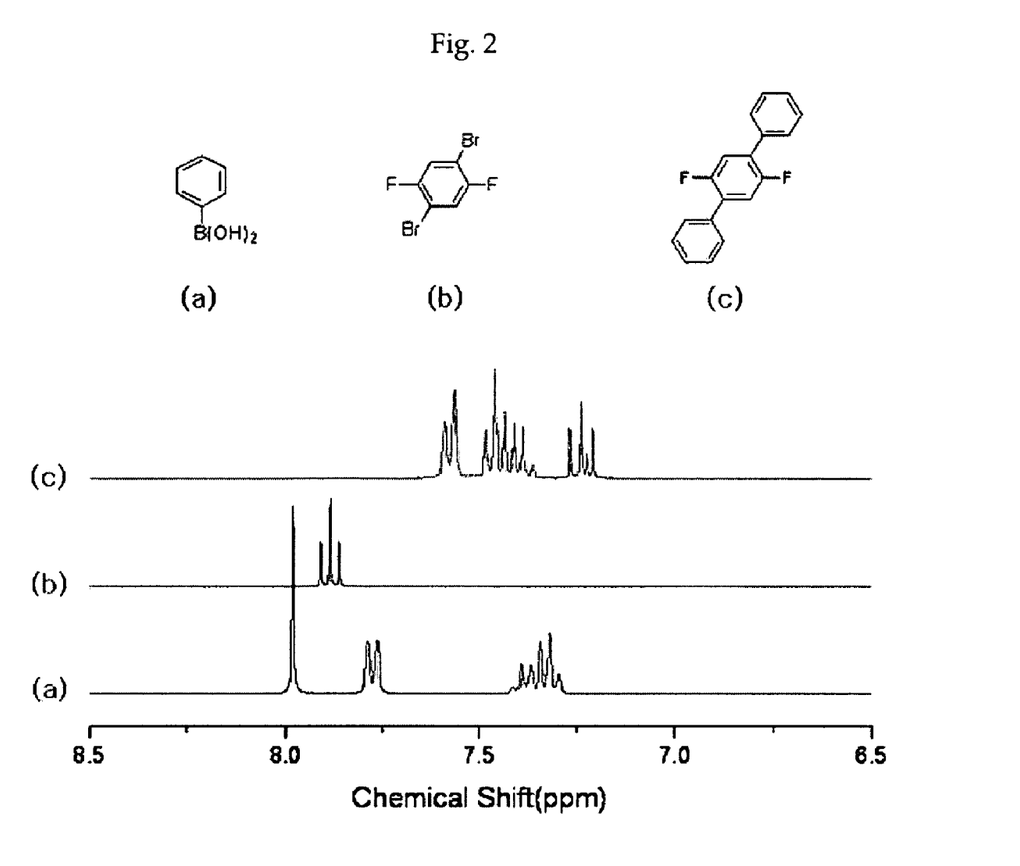
FIG. 2 shows $^1$H-NMR spectra of phenylboronic acid, 1,4-dibromo-2,5-difluorobenzene and TPDF.

The final product was in the form of white needle-like crystal and had a melting point of 158.5–159.2° C. Structural analysis was performed by GC-Mass, $^1$H-NMR and $^{13}$C-NMR. As seen in the GC-Mass spectrum of FIG. 1, the parent ion was prominent at 266. The $^1$H-NMR spectra of FIG. 2 show that the boronic acid peak disappeared after the reaction. Also, they show up-field shift of the hydrogen peak of the benzene ring of phenylboronic acid from 7.78 ppm to 7.58 ppm and up-field shift of the hydrogen peak of 1,4-dibromo-2,5-difluorobenzene from 7.89 ppm to 7.24 ppm. It is because the electron density in the protons increased by the resonance of the benzene rings. Synthesis of TPDF can be also confirmed from the bcm mode and dept-135 mode $^{13}$C-NMR spectra of FIG. 3. From the above analyses, it is clear that the Suzuki cross-coupling reaction was performed successfully.

Example 2

4,4"-Disulfonated-2',5'-difluoro-[1,1':4',1"]terphenyl (STPDF)

To a 2-necked round flask equipped with a condenser, a dropping funnel and a magnetic stir bar and substituted with nitrogen, 2',5'-difluoro-[1,1':4',1"]terphenyl (3.755 mmol) and dichloromethane (10 mL) were added. Then, chlorosulfonic acid (0.6 mL) was slowly added through the dropping funnel for 1 hour. Reaction was performed under nitrogen atmosphere at room temperature for 5 hours. Precipitate formed in the reactor during the reaction was filtered to obtain 4,4"-disulfonyl chloride-2',5'-difluoro-[1,1':4',1"]terphenyl. The filtered 4,4"-disulfonyl chloride-2',5'-difluoro-[1,1':4',1"]terphenyl was dried under vacuum at 40° C. and dissolved again in ice water. Then, a 2M sodium hydroxide solution was added to induce precipitation. Upon completion of the reaction, the reaction mixture was filtered to obtain 4,4"-disulfonated-2',5'-difluoro-[1,1':4',1"]terphenyl. The product was dried under vacuum at 40° C. The yield was relatively high (≧82%).

Figure 3:
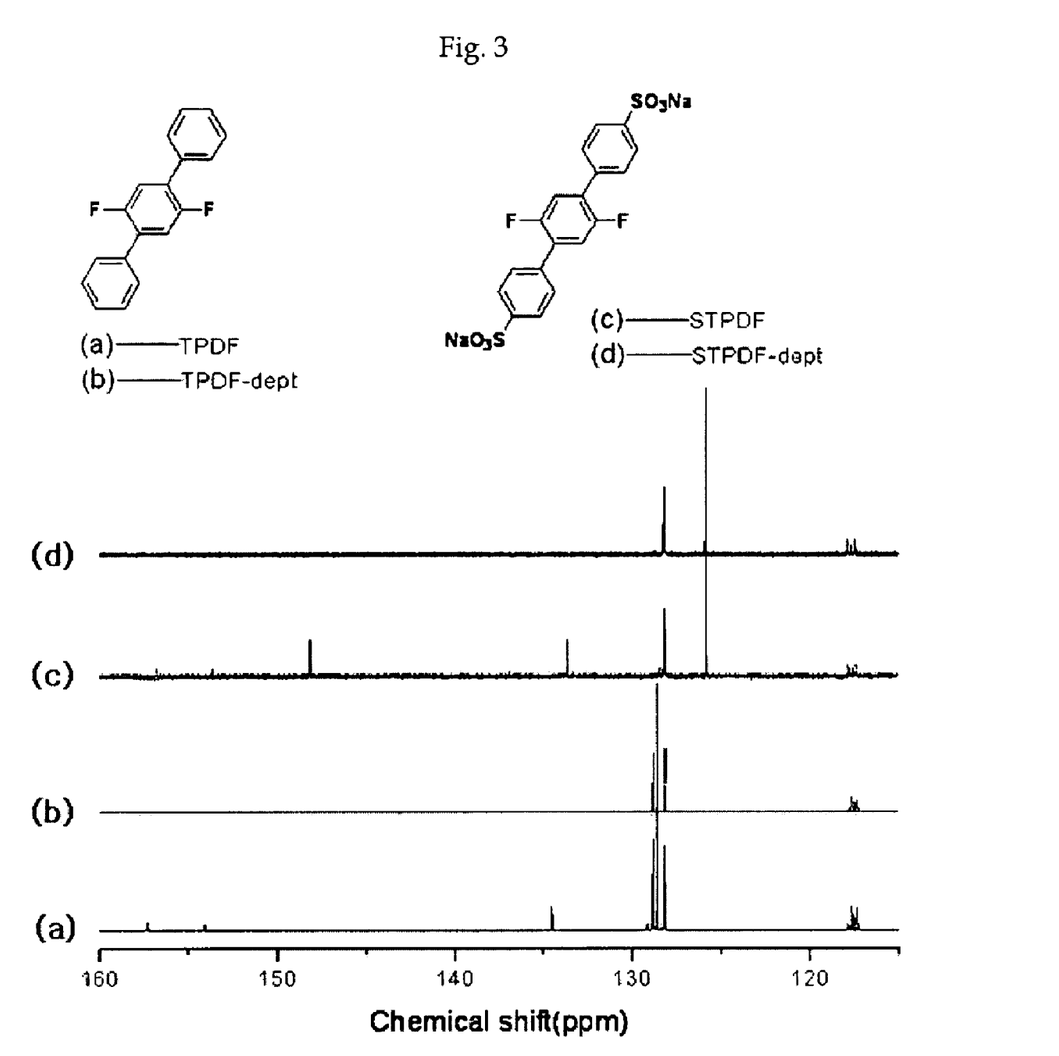
FIG. 3 shows $^{13}$C-NMR spectra of TPDF and STPDF at bcm mode and 135dept mode.
Figure 4:
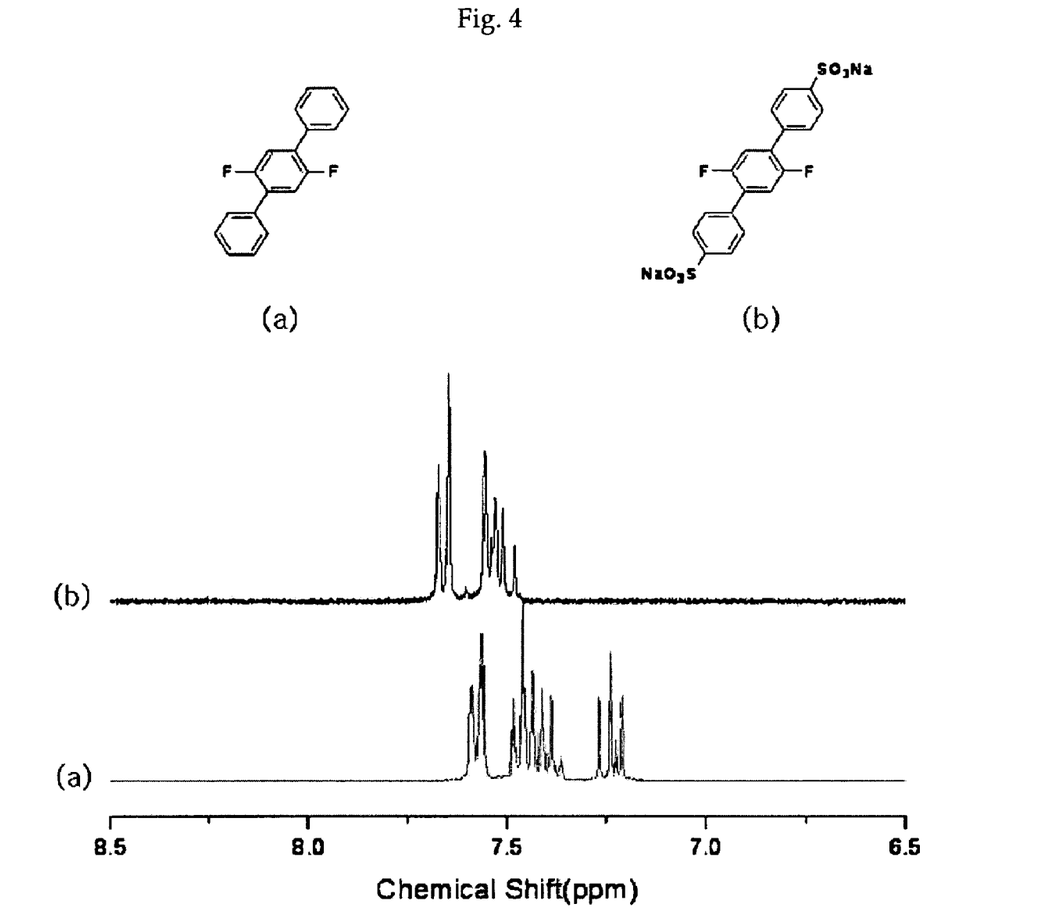
FIG. 4 shows $^1$H-NMR spectra of TPDF and STPDF.
Figure 5:
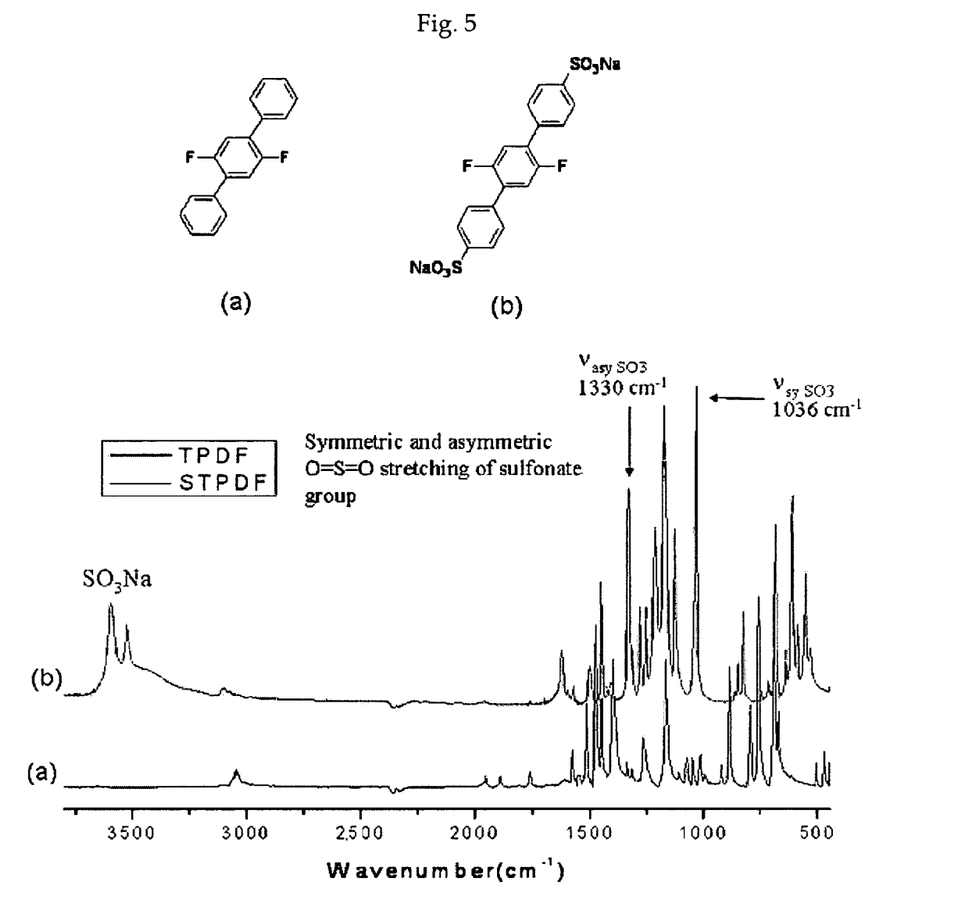
FIG. 5 shows FT-IR spectra of TPDF and STPDF.
Figure 6:
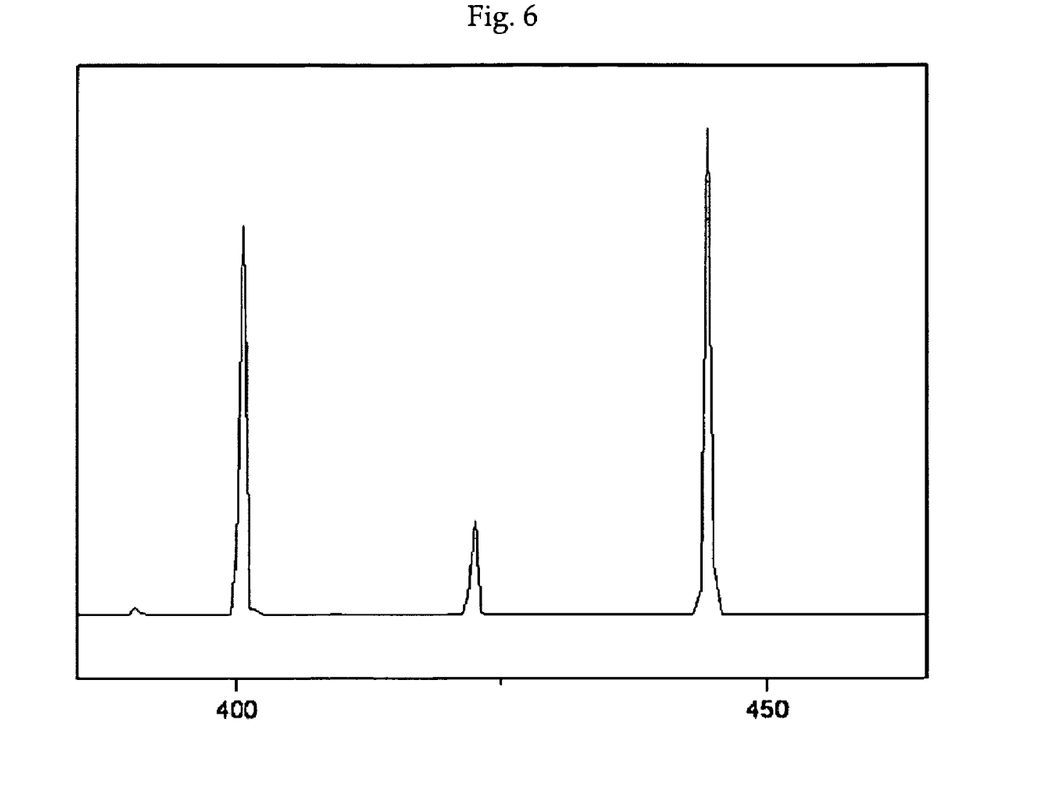
FIG. 6 shows a MALDI-TOF Mass spectrum of STPDF.

The final product was in the form of powdery white solid. Structural analysis was performed by $^1$H-NMR, $^{13}$C-NMR, FT-IR, MALDI-TOF Mass and EA (element analysis). As seen in the $^1$H-NMR spectra of FIG. 4, all the hydrogen peaks showed a down-field shift and the hydrogen peak of TPDF at 7.39 ppm disappeared, which confirms the introduction of the sulfonate group. The integration values of the peak were also assigned exactly. The bcm mode and dept-135 mode $^{13}$C-NMR spectra of FIG. 3 show down-field shift from 128.2 ppm to 148.2 ppm, which is due to the decrease of electron density caused by the electron withdrawing effect of the sulfonate group. The disappearance of the peak at 148.2 ppm also confirms the synthesis of STPDF. The FT-IR spectra of FIG. 5 also shows symmetric and asymmetric stretching vibration of the sulfonate group assigned at 1036, 1330, respectively. And vibrational stretching peak around 3500 cm$^{-1}$ of the sulfonate group was confirmed. The MALDI-TOF Mass spectrum of FIG. 6 shows mass peaks at 445 and 422.5, which correspond to the molecular weight subtracting that of Na and 2Na, respectively. The EA analysis showed a composition of C (45.9%), H (3.98%) and S (13.03%), which is similar to the theoretical value of C (45.96%), H (2.14%) and S (13.63%). From the above analyses, it is clear that the Suzuki cross-coupling reaction was performed successfully.

Example 3

4',5'-Difluoro-[1,1':2',1"]terphenyl (DFTP)

Suzuki cross-coupling reaction was performed in the same manner as in Example 1, except that 1,2-dibromo-4,5-difluorobenzene was used instead of 1,4-dibromo-2,5-difluorobenzene as starting material. The yield was high (≧92%).

Figure 7:
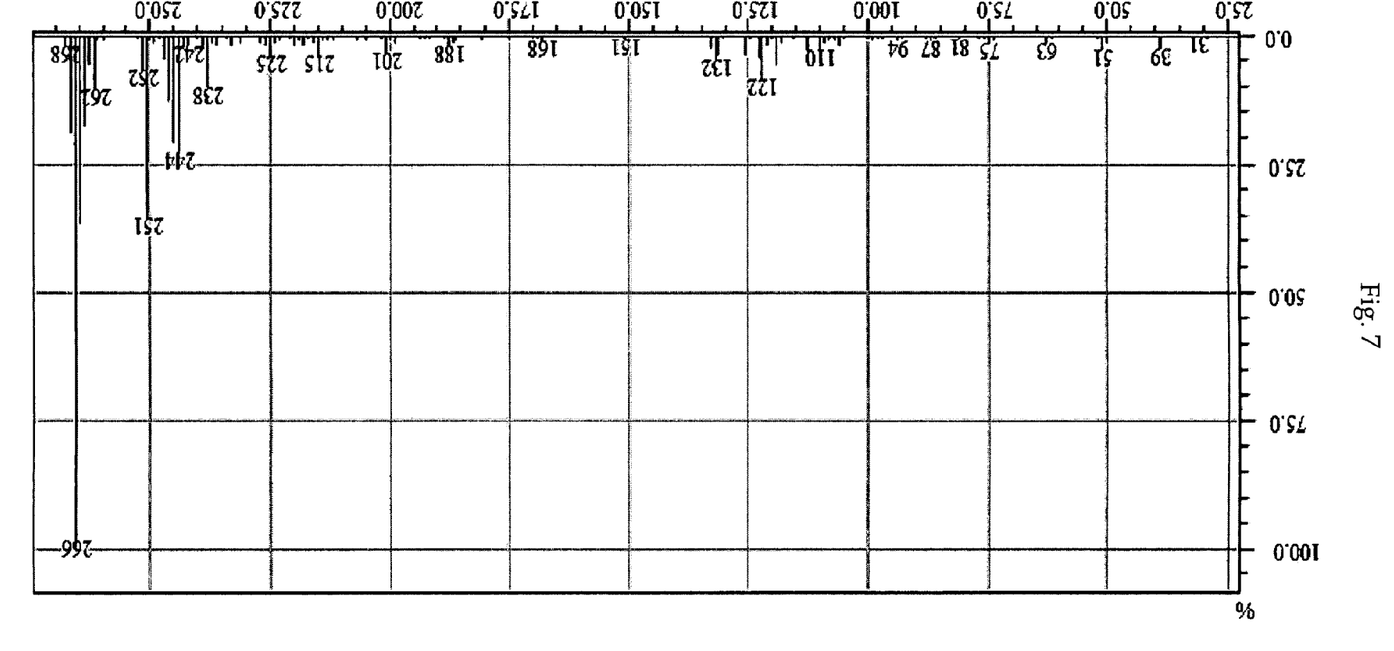
FIG. 7 shows a GC-Mass spectrum of DFTP.
Figure 8:
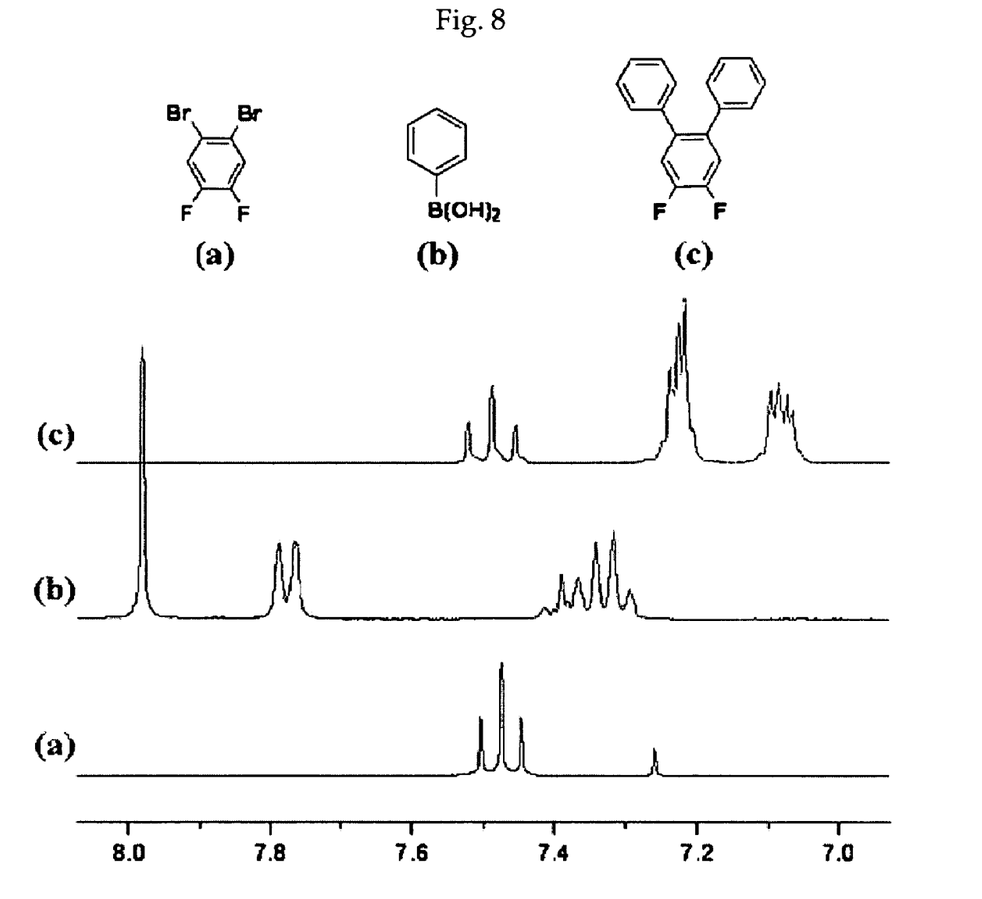
FIG. 8 shows $^1$H-NMR spectra of phenylboronic acid, 1,2-dibromo-4,5-difluorobenzene and DFTP.
Figure 9:
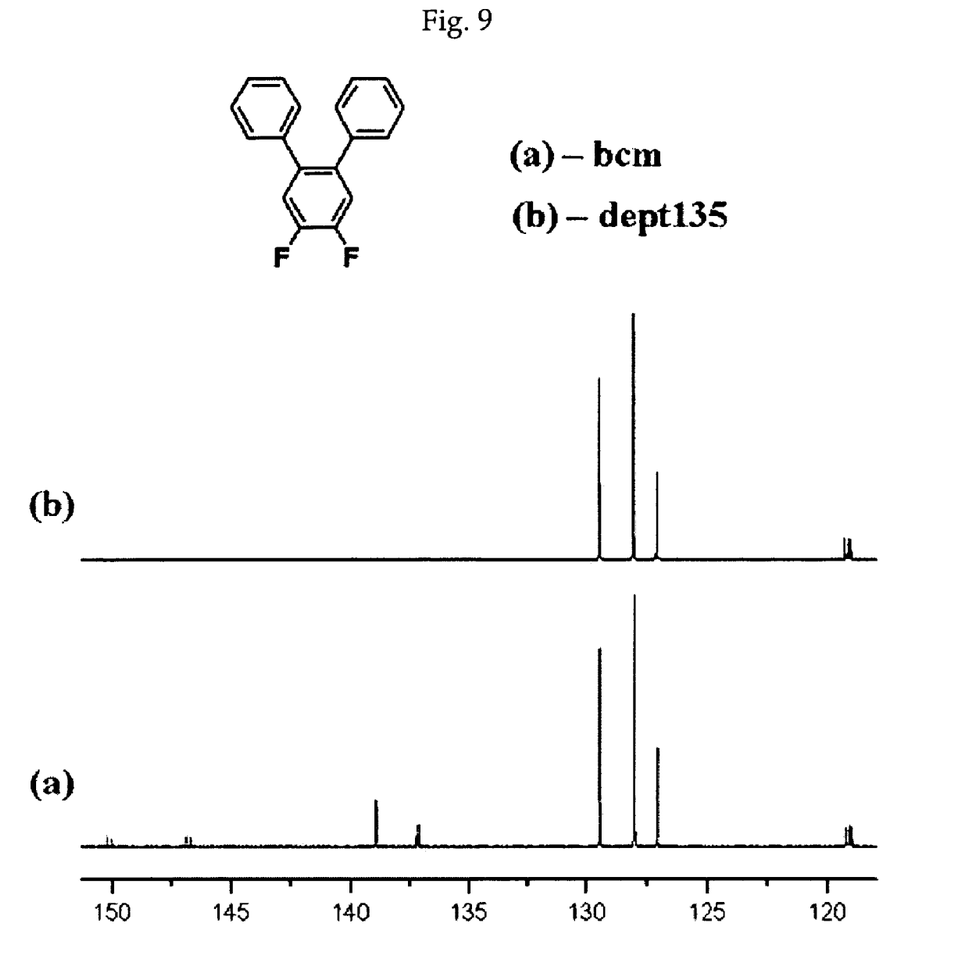
FIG. 9 shows $^{13}$C-NMR spectra of DFTP at bcm mode and 135dept mode.

The final product was in the form of white needle-like crystal and had a melting point of 93.5–94.3° C. Structural analysis was performed by GC-Mass, $^1$H-NMR and $^{13}$C-NMR. As seen in the GC-Mass spectrum of FIG. 7, the parent ion was prominent at 266. The $^1$H-NMR spectra of FIG. 8 show that the boronic acid peak disappeared after the reaction. Also, they show up-field shift of the hydrogen peak of the benzene ring of phenylboronic acid from 7.78 ppm to 7.09 ppm and up-field shift of the hydrogen peaks around 7.34 ppm (peaks of four hydrogens of phenylboronic acid) to around 7.23 ppm. It is because the electron density in the protons increased due to the resonance of the benzene rings, as explained in Example 1. Further, the hydrogen peak area coincided exactly. Synthesis of DFTP can also be confirmed from the bcm mode and dept-135 mode $^{13}$C-NMR spectra of FIG. 9. From the above analyses, it is clear that the Suzuki cross-coupling reaction was performed successfully.

Example 4

4,4"-Disulfonated-4',5'-difluoro-[1,1':2',1"]terphenyl (SDFTP)

Sulfonate substitution was performed in the same manner as in Example 2, except that 4',5'-difluoro-[1,1':2',1"]terphenyl was used instead of 2',5'-difluoro-[1,1':4',1"]terphenyl as starting material. The yield was high (≧80%).

Figure 10:
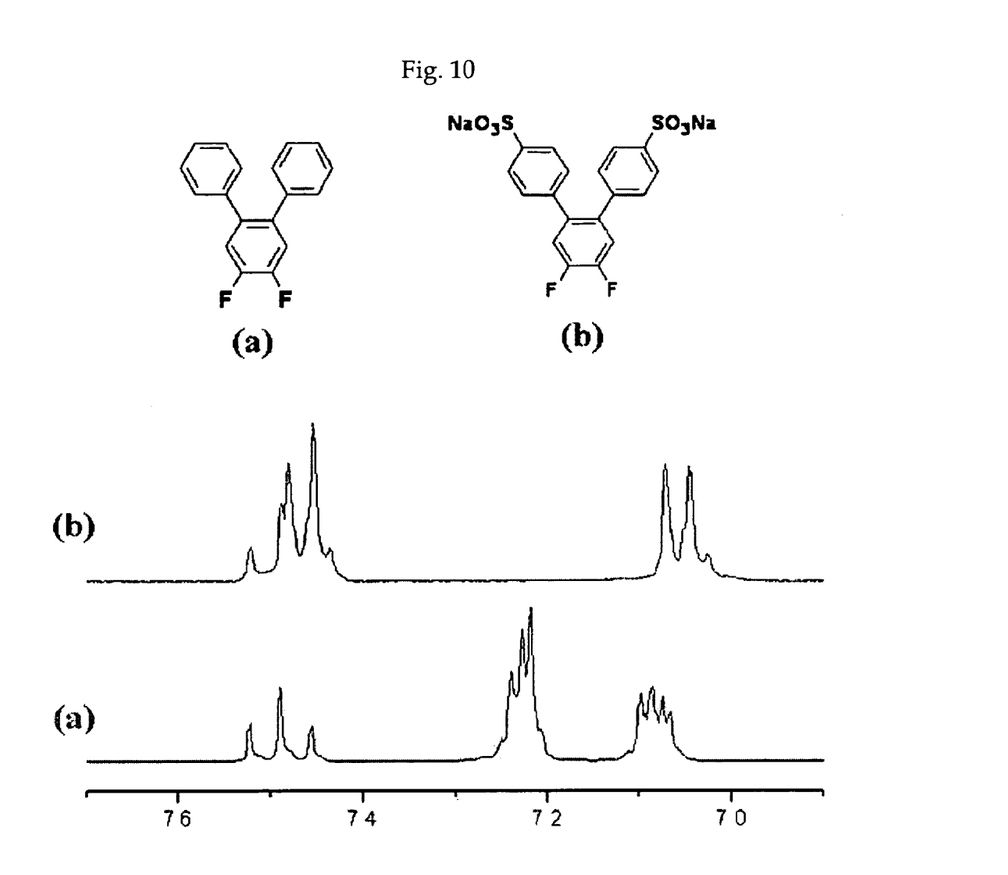
FIG. 10 shows $^1$H-NMR spectra of DFTP and SDFTP.
Figure 11:
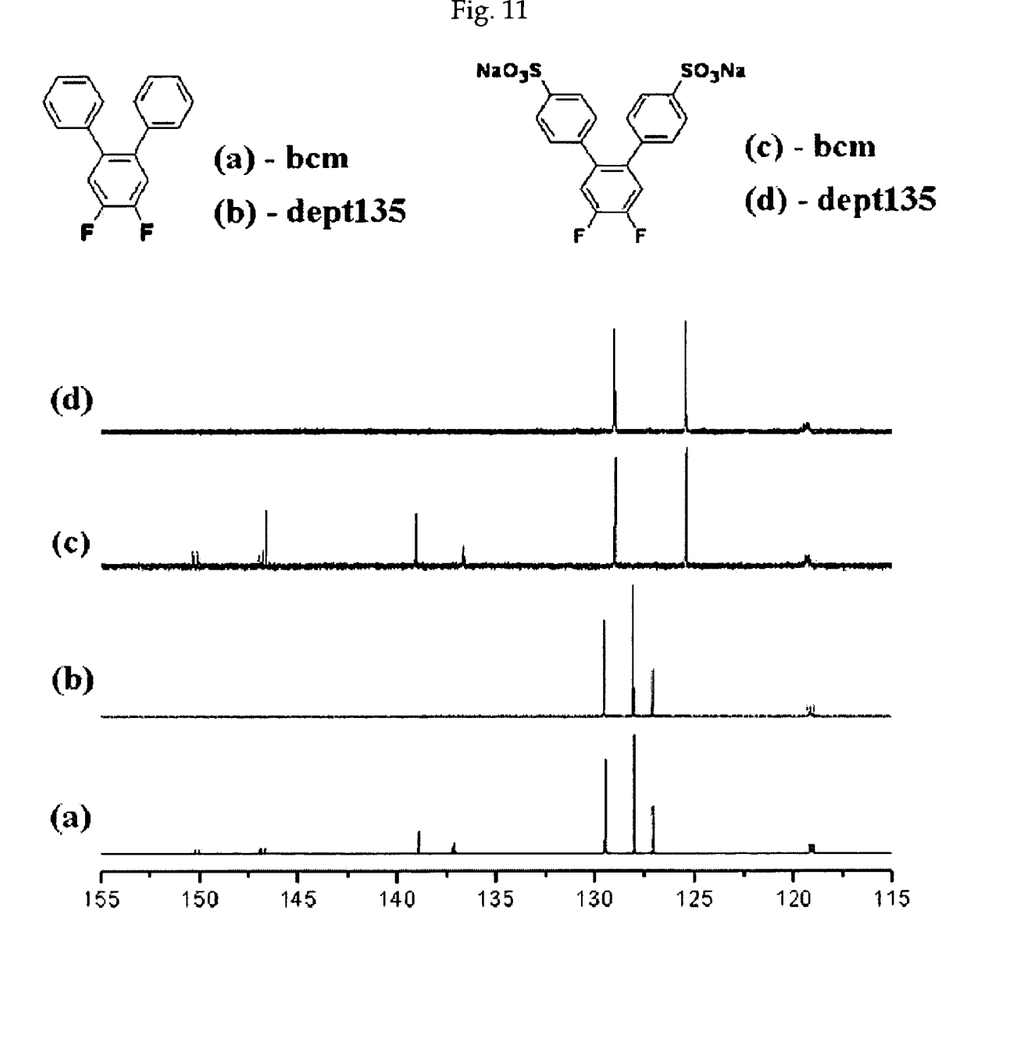
FIG. 11 shows $^{13}$C-NMR spectra of DFTP and SDFTP at bcm mode and 135dept mode.
Figure 12:
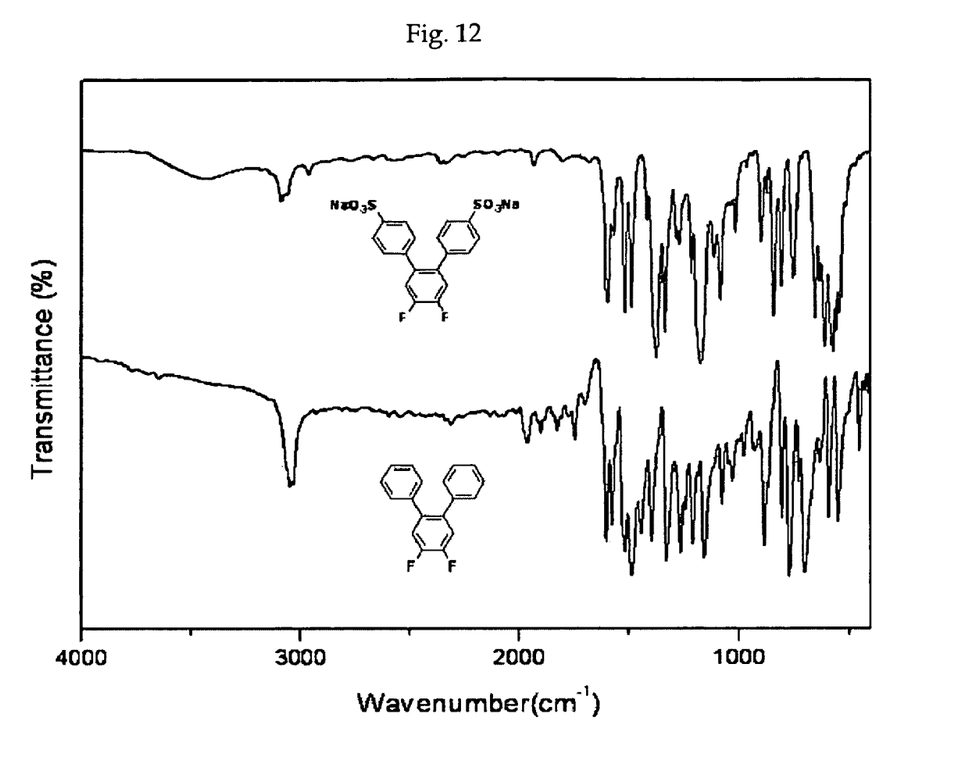
FIG. 12 shows FT-IR spectra of DFTP and SDFTP.

The final product was in the form of powdery white solid. Structural analysis was performed by $^1$H-NMR, $^{13}$C-NMR, FT-IR, MALDI-TOF Mass and EA. As seen in the $^1$H-NMR spectra of FIG. 10, the peak of the hydrogen neighboring the sulfonate group shifted down-field from 7.23 ppm to 7.49 ppm because of the electron withdrawing effect of the group. The hydrogen peak area coincided exactly. The bcm mode and dept-135 mode $^{13}$C-NMR spectra of FIG. 11 show down-field shift from 124 ppm to 146.7 ppm, which is due to the decrease of electron density caused by the electron withdrawing effect of the sulfonate group. The disappearance of the peak at 146.7 ppm also confirms the synthesis of SDFTP. The FT-IR spectra of FIG. 12 also shows symmetric and asymmetric stretching vibration of the sulfonate group assigned at 1014, 1110, respectively. And vibrational stretching peak around 3500 cm$^{-1}$ of the sulfonate group was confirmed. The EA analysis showed a composition of C (45.89%), H (2.98%) and S (13.27%), which is similar to the theoretical value of C (45.96%), H (2.14%) and S (13.63%). From the above analyses, it is clear that the Suzuki cross-coupling reaction was performed successfully.

INDUSTRIAL APPLICABILITY

Due to the structural characteristic of the terphenyl dihalide monomer having sulfonate groups represented by the formula (1) in accordance with the present invention, polymer electrolyte membranes prepared from the novel monomer have thermal stability and chemical stability comparable to those of poly(arylene ether)s, are easily processed and absorb less moisture, making them applicable for use in thermoplastic polymers, membrane elastomers, and the like. Because of the sulfonate groups, the polymers have good proton conductivity even with low moisture content and have good dimensional stability even when exposed to moisture for an extended period of time. Therefore, they provide excellent properties as polymer electrolyte membranes and are expected to be useful for manufacturing fuel cells or secondary cells.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the present invention as set forth in the appended claims.

The invention claimed is:

1. A terphenyl dihalide monomer having sulfonate groups represented by the formula (1) below:

wherein $X^1$ and $X^2$ are independently F or Cl; and $M^1$ and $M^2$ are independently an alkali metal atom.

2. The monomer represented by the formula (1) as set forth in claim 1, which is selected from the group consisting of 4,4"-disulfonated-2',5'-difluoro-[1,1':4',1"]terphenyl and 4,4"-disulfonated-4',5'-difluoro-[1,1':2',1"]terphenyl.

3. A process for preparing a terphenyl dihalide monomer having sulfonate groups represented by the formula (1) below comprising:
preparing a terphenyl dihalide derivative represented by the formula (2) below by Suzuki cross-coupling of a tetrahalobenzene represented by the formula (3) below and phenylboronic acid; and
introducing sulfonate groups into the phenyl rings at each end of the terphenyl dihalide derivative represented by the formula (2), wherein $X^1$ and $X^2$ are independently F or Cl; $Y^1$ and $Y^2$ are independently Br or I; and $M^1$ and $M^2$ are independently an alkali metal atom.

4. The preparation process as set forth in claim 3, wherein the tetrahalobenzene represented by the formula (3) is 1,2-dibromo-4,5-difluorobenzene or 1,4-dibromo-2,5-difluorobenzene.

5. The preparation process as set forth in claim 3, wherein a sulfonate compound selected from strong sulfuric acid, chlorosulfonic acid (ClSO$_3$H), fuming sulfuric acid (SO$_3$.H$_2$SO$_4$) and fuming sulfuric acid triethylphosphate (SO$_3$.TEP) is used in the introduction of the sulfonate group.

* * * * *